United States Patent
Han et al.

(10) Patent No.: US 11,562,549 B2
(45) Date of Patent: Jan. 24, 2023

(54) SYSTEM AND METHOD FOR USER INTERACTION IN COMPLEX WEB 3D SCENES

(71) Applicant: SHENZHEN JINGTAI TECHNOLOGY CO., LTD., Guangdong (CN)

(72) Inventors: Fei Han, Guangdong (CN); Yan Wang, Guangdong (CN); Jian Ma, Guangdong (CN); Lipeng Lai, Guangdong (CN); Shuhao Wen, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 17/252,737

(22) PCT Filed: Dec. 20, 2019

(86) PCT No.: PCT/CN2019/126991
§ 371 (c)(1),
(2) Date: Dec. 16, 2020

(87) PCT Pub. No.: WO2021/004020
PCT Pub. Date: Jan. 14, 2021

(65) Prior Publication Data
US 2021/0375063 A1  Dec. 2, 2021

(51) Int. Cl.
*G16C 20/80* (2019.01)
*G06T 19/20* (2011.01)
(Continued)

(52) U.S. Cl.
CPC ............. *G06T 19/20* (2013.01); *G06F 40/14* (2020.01); *G06T 17/00* (2013.01); *G16C 20/30* (2019.02); *G06T 2219/2012* (2013.01)

(58) Field of Classification Search
CPC . G06T 19/20; G06T 17/00; G06T 2219/2012; G06F 40/14; G16C 20/30
See application file for complete search history.

(56) References Cited

U.S. PATENT DOCUMENTS

| | | | |
|---|---|---|---|
| 6,522,632 B1 * | 2/2003 | Waters | G06F 16/9566 370/254 |
| 7,996,156 B2 * | 8/2011 | Beger | G01N 33/48 703/2 |

(Continued)

FOREIGN PATENT DOCUMENTS

| CN | 103885788 | 6/2014 |
|---|---|---|
| CN | 104537705 | 4/2015 |

(Continued)

OTHER PUBLICATIONS

Rose et al., NGL Viewer: a web application for molecular visualization, 2015 (Year: 2015).*

(Continued)

*Primary Examiner* — Phong X Nguyen
(74) *Attorney, Agent, or Firm* — Muncy, Geissler, Olds & Lowe, P.C.

(57) ABSTRACT

This disclosure provides a system and method for user interaction in complex web 3D scenes, including a receiving module, a transmission module and a 3D model module. The receiving module receives molecular data. The transmission module analyzes the received molecular data and then enters the two branch modules at the same time. The branch modules include: a view layer unit: processing browser rendering and 3D model construction, the data generated by the branch will finally be presented on the browser page; a data layer unit: processing 3D picking-related business logic, and establishing a list of related model index information for atoms and covalent bonds in molecular data. The 3D model module: establishes a one-to-one correspondence (Continued)

between color and 3D model. This invention simplifies the display model of the molecule for the picking of web 3D molecular visualization and reduces the computational cost of the model data on the rendering.

3 Claims, 6 Drawing Sheets

(51) Int. Cl.
*G16C 20/30* (2019.01)
*G06F 40/14* (2020.01)
*G06T 17/00* (2006.01)

(56) References Cited

U.S. PATENT DOCUMENTS

| | | | | |
|---|---|---|---|---|
| 8,706,316 | B1* | 4/2014 | Hoevenaar | G07C 5/0825 |
| | | | | 701/1 |
| 10,372,713 | B1* | 8/2019 | Blake | G06N 3/088 |
| RE48,155 | E* | 8/2020 | Lee | G06F 1/1677 |
| 11,209,863 | B2* | 12/2021 | Delaporte | G06F 1/1643 |
| 2006/0227241 | A1* | 10/2006 | Dyke | H04N 9/74 |
| | | | | 348/384.1 |
| 2008/0234996 | A1* | 9/2008 | Ghosh | G16B 15/30 |
| | | | | 703/12 |
| 2009/0024575 | A1* | 1/2009 | Wagner | G16C 20/10 |
| 2011/0276589 | A1* | 11/2011 | Smith | G06V 30/422 |
| | | | | 707/769 |
| 2013/0215041 | A1* | 8/2013 | Kim | G06F 3/1446 |
| | | | | 345/173 |
| 2013/0286038 | A1* | 10/2013 | Kamath | G06T 7/0012 |
| | | | | 345/592 |
| 2013/0300656 | A1* | 11/2013 | Roegelein | G06F 11/3664 |
| | | | | 345/157 |
| 2013/0342509 | A1* | 12/2013 | Kang | G06F 3/0416 |
| | | | | 345/174 |
| 2014/0098095 | A1* | 4/2014 | Lee | G06F 3/041 |
| | | | | 345/420 |
| 2014/0218321 | A1* | 8/2014 | Lee | G06F 1/1677 |
| | | | | 345/173 |
| 2014/0258817 | A1* | 9/2014 | Carrier | G06F 40/103 |
| | | | | 715/202 |
| 2014/0282106 | A1* | 9/2014 | Smith | G06F 3/017 |
| | | | | 715/753 |
| 2014/0301608 | A1* | 10/2014 | Karthikeyan | G06V 30/262 |
| | | | | 382/113 |
| 2014/0375530 | A1* | 12/2014 | Delaporte | G06F 1/1652 |
| | | | | 345/1.3 |
| 2015/0142730 | A1* | 5/2015 | Dakshanamurthy | G16H 70/40 |
| | | | | 707/769 |
| 2016/0232856 | A1* | 8/2016 | Hidaka | G06F 3/147 |
| 2017/0286457 | A1* | 10/2017 | Natarajan | G06F 16/248 |
| 2018/0330480 | A1 | 11/2018 | Liu et al. | |
| 2019/0278757 | A1* | 9/2019 | Palmer | G06F 16/2379 |
| 2020/0066022 | A1* | 2/2020 | Leong | G06F 3/0482 |
| 2020/0372875 | A1* | 11/2020 | Iyer | G06F 3/0346 |
| 2021/0150953 | A1* | 5/2021 | Lee | G09G 3/035 |
| 2021/0375063 | A1* | 12/2021 | Han | G16C 20/30 |
| 2021/0403428 | A1* | 12/2021 | Buckley | C07D 213/80 |

FOREIGN PATENT DOCUMENTS

| | | |
|---|---|---|
| CN | 108763472 | 11/2018 |
| CN | 109658992 | 4/2019 |
| CN | 111192641 | 5/2020 |

OTHER PUBLICATIONS

Bernier et al., RiboVision Suite for Visualization and Analysis of Ribosomes, 2014 (Year: 2014).*
Mwalongo et al., Remote Visualization of Dynamic Molecular Data using WebGL, 2015 (Year: 2015).*
Jonsson et al., Inviwo—A Visualization System with Usage Abstraction Levels, 2019 (Year: 2019).*
"International Search Report (Form PCT/ISA/210)" of PCT/CN2019/126991, dated Sep. 23, 2020, pp. 1-5.
Written Opinion of the International Searching Authority (Form PCT/CN2019/126991, dated Sep. 23, 2020, pp. 1-4.

* cited by examiner

SYSTEM AND METHOD FOR USER INTERACTION IN COMPLEX WEB 3D SCENES

CROSS-REFERENCE TO RELATED APPLICATION

This application is a 371 of international application of PCT application serial no. PCT/CN2019/126991, filed on Dec. 20, 2019. The entirety of each of the above mentioned patent application is hereby incorporated by reference herein and made a part of this specification.

FIELD OF THE INVENTION

The invention pertains to the field of chemical computing. It concerns a system and method for user interaction in complex web 3D scenes.

BACKGROUND OF THE INVENTION

In the field of chemical research, it is often necessary to have a set of standard description files for molecules (mol format) and crystals (cif format) to facilitate different research organizations and institutions to reach a consensus on chemical molecules or crystals of the same structure. But the data in plain text format such as cif and mol is not conducive to the intuitive observation of the 3D structure of the corresponding chemical structure. Although there is related 3D structure display software in the chemistry field, these client end application is not conducive to popularization and dissemination. With the improvement of modern browser performance and the update of web 3D technology, web 3D tools that can run 3D display and interaction in browser have been developed base on JavaScript-based programming language.

Due to the complex structure of many chemical molecules or crystals, a large amount of data calculations will be needed during 3D rendering, so performance optimization is particularly important. The purpose of this solution is to solve the problems of stuttering and insufficient rendering frame rate caused by time-consuming calculation on the 3D molecular visualization interaction in the browser environment.

The current interactive operations in the web 3D scene are first based on the click picking up of objects in the 3D scene. At present, the main solution for picking up objects in a 3D scene is ray picking.

Figure 1:
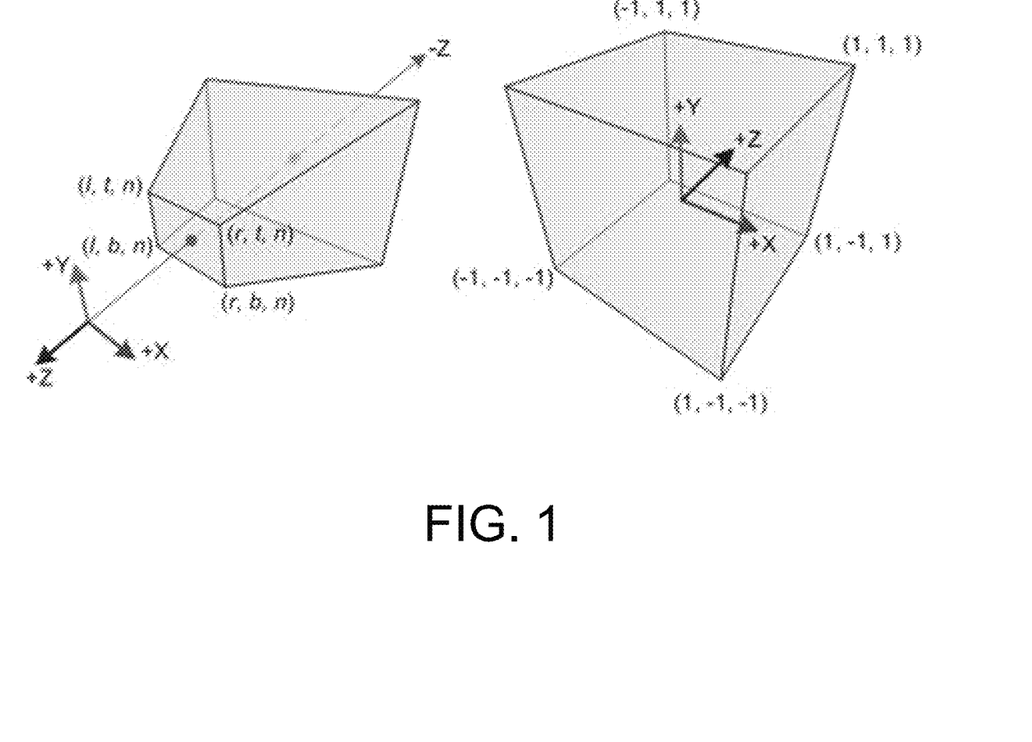
FIG. 1 is a visual cone model under perspective projection in the prior art.
Figure 2:
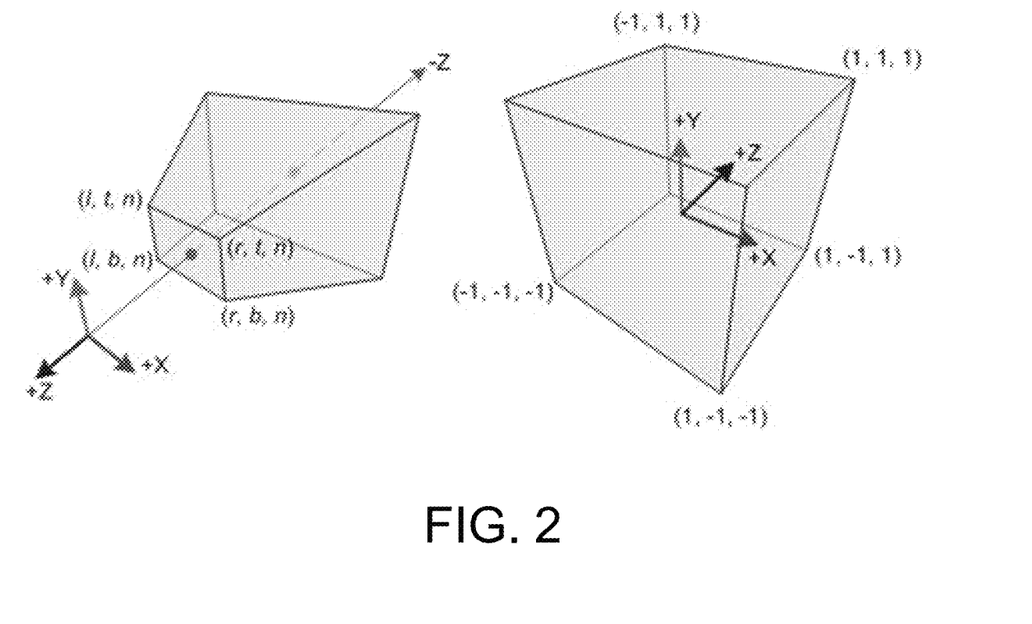
FIG. 2 is a visual cone model under orthogonal projection in the prior art.
Figure 3:
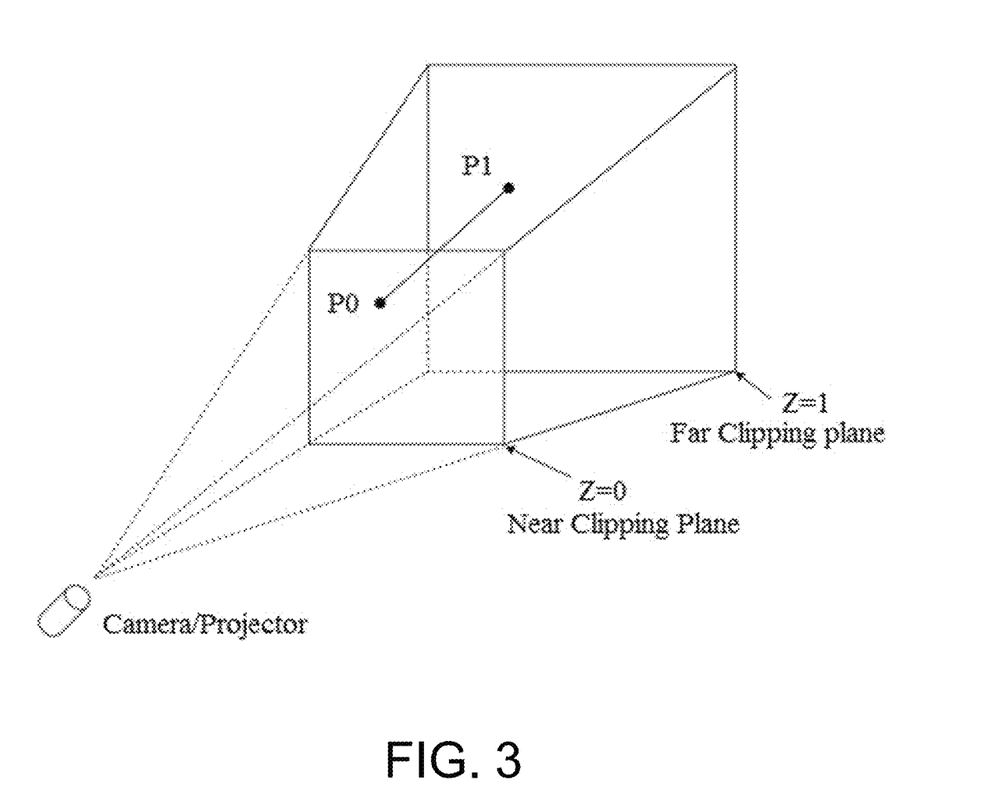
FIG. 3 is a visual cone of prospective projection.

The objects rendered by the webgl rendering engine are located in a space called the frustum, as shown in FIG. 1 and FIG. 2.

SUMMARY OF THE INVENTION

In order to solve the above technical problems, this invention provides a system for user interaction in complex web 3D scenes, including a receiving module, a transmission module and a 3D model module.

The receiving module: receives molecular data, mol files, cif files, and a custom structure containing crystal information;

The transmission module: analyzes the received molecular data and then enters two branch modules at the same time.

The branch modules include:

A view layer unit: handles the rendering of the browser and the 3D model construction, and the data generated by this branch will finally be presented on the browser page.

A data layer unit: processes 3D picking-related business logic, and establishes a list of related model index information on atoms, covalent bonds, hydrogen bonds, and flexible angles in molecular data.

The 3D model module: establishes a one-to-one correspondence between color and 3D mode. And all 3D models that need to be picked up have a unique index in the data layer.

Preferably, the molecular data adopts mol file, cif file, and a custom structure containing crystal information.

Correspondingly, this invention provides a method for user interaction in complex web 3D scenes, which includes the following steps.

Step A: analyze the molecular data after receiving it.

Step B: then it will enter two branch modules at the same time, including the first branch module and the second branch module. The first branch module serves as the view layer, mainly processing browser rendering and 3D model construction, and the data generated by the branch will finally be presented on the browser page.

Step C: The second branch module is used as data layer, specifically responsible for processing 3D pickup-related business logic, and establishes a list of related model index information on atoms and covalent bonds in molecular data.

Step D: Establish corresponding simplified model data in an invisible 3D scene according to request, and establish a one-to-one correspondence between color and 3D model. All 3D models that need to be picked will have a unique index in the data layer.

Wherein, the index is a hexadecimal color, which ranges from #000001 to #FFFFFE that mark a total of 16*16*16*16*16*16-2 units, and without rendering on the browser page.

This invention brings the following beneficial effects.

1. This solution firstly simplifies the display model (Stick-shaped model) of the molecule and reduces the computational cost of rendering the model data for Web 3D molecular visualization picking.

2. By establishing a simplified pickable model data of a data layer that does not need to be rendered, the overhead of 3D scene rendering is reduced, and the construction of unnecessary picking model data is avoided.

BRIEF DESCRIPTION OF THE DRAWINGS

In FIG. 5, L2 represents the relevant data of the 3D scene rendered in the browser page, which corresponds to the data generated by the view layer in FIG. 1. L1 can be regarded as a computer screen.

DESCRIPTION OF THE PREFERRED EMBODIMENT

The preferred embodiments of this invention will be further described in detail below in conjunction with the accompanying drawings.

Embodiment 1

Figure 4:
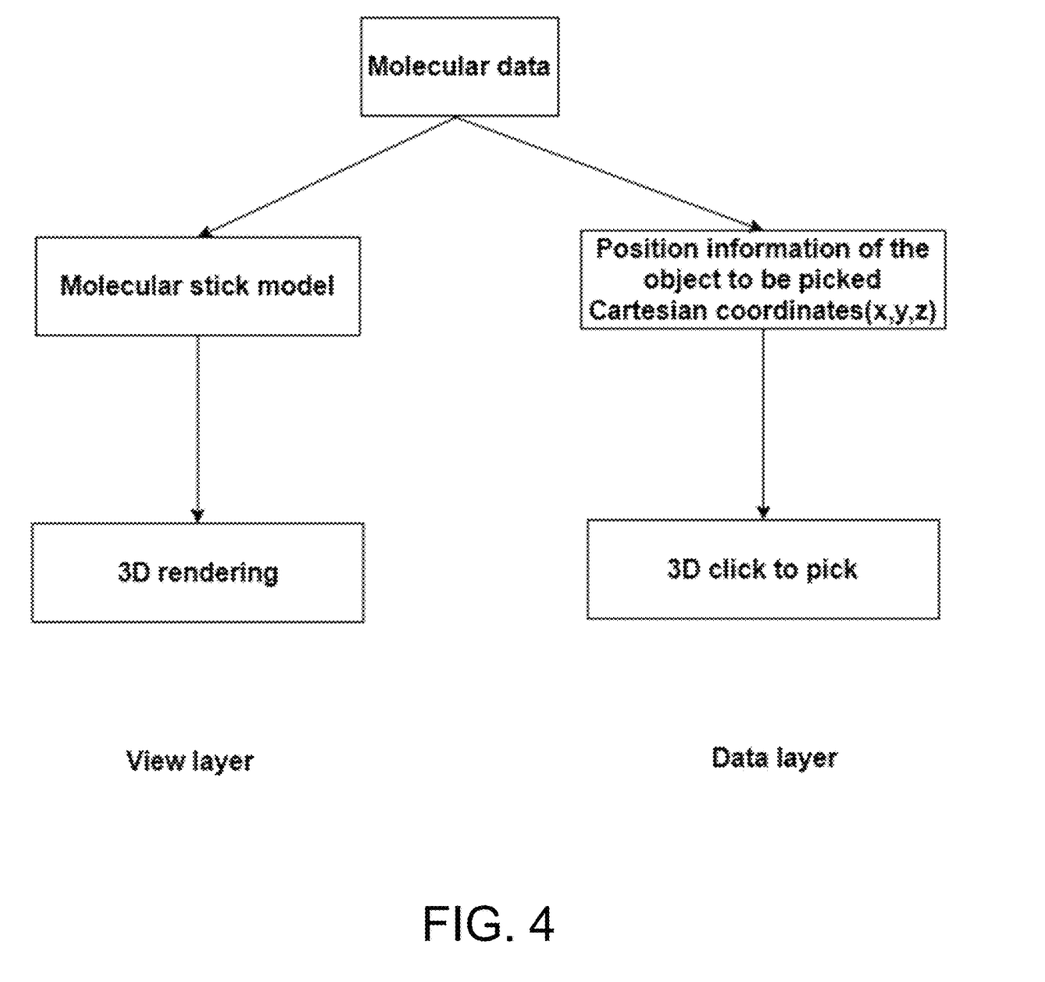
FIG. 4 shows the process flow of the 3D picking scheme

FIG. 4 shows the process flow of the 3D picking scheme, wherein the molecular data (mol, cif files) is analyzed after received and then enters two branch modules at the same time. The branch module on the left is used as the view layer, which mainly deals with the rendering of the browser and the construction of the 3D model. The data generated by this branch will finally be presented on the browser page; while the branch module on the right is used as the data layer and is responsible for processing 3D Pick up relevant business logic, and establishing a list of index information of related models on atoms and covalent bonds in molecular data. The data generated by this branch module is always operated in memory and would establish a corresponding simplified model data in an invisible 3D scene and a one-to-one correspondence between color and 3D model. All 3D models that need to be picked up will have a unique index in the data layer, wherein, the index is a hexadecimal color, which ranges from #000001 to #FFFFFE that marks a total of 16*16*16*16*16-2 units without rendering on the browser page.

Embodiment 2

Figure 5:
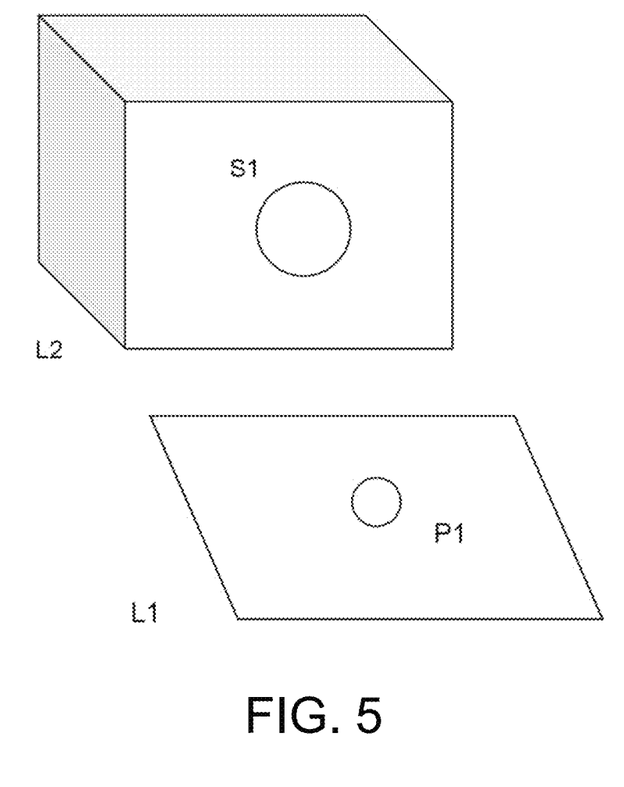
Figure 6:
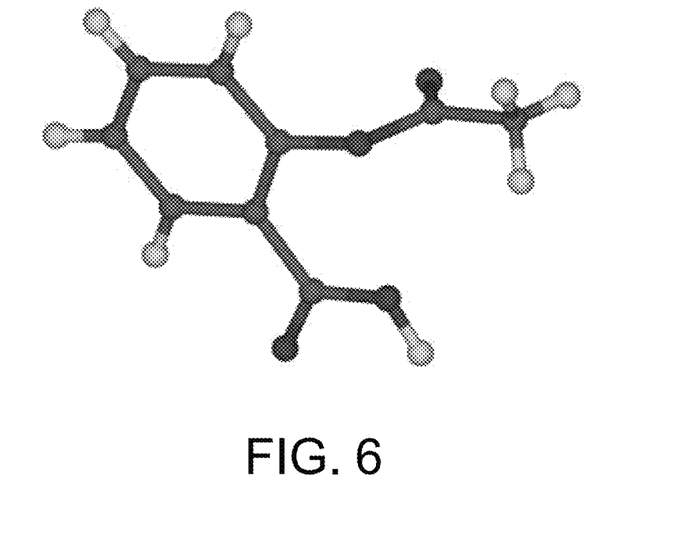
FIG. 6-9 is the effect diagram of the present invention.

As shown in FIG. 5, L2 represents the relevant data of the 3D scene rendered in the browser page, which corresponds to the data generated by the view layer in FIG. 4. L1 can be regarded as a computer screen. When the user clicks on the point P1 on the screen, a 3D picking operation is triggered. When the user clicks on the point P1 on the screen, the pick-up module will obtain the screen click position of this point and construct a temporary virtual plane. This plane is similar to the computer screen L1. The plane is the projection of the 3D model data on the 2D plane. Just as the sphere S1 is projected on L1 as a circle P1, the projected 2D shapes on the virtual plane use the index of the projected 3D model as their own color. For example, the index of an atom in the pickup module in 3D space is #123456, and then on the virtual plane temporarily constructed by the pickup module, the color of the circle where the atom is mapped on the plane is #123456. After the community module reads the color #123456 of the mouse position on the virtual plane, the 3D model corresponding to the position was found without calculation by using the color as the index, and the 3D object information at that point was successfully picked up. In this way, a large number of calculation processes can be avoided, and at the same time, the cost of data calculation of the 3D model that does not need to be picked up is reduced, thereby improving the rendering frame rate of the 3D scene.

Figure 7:
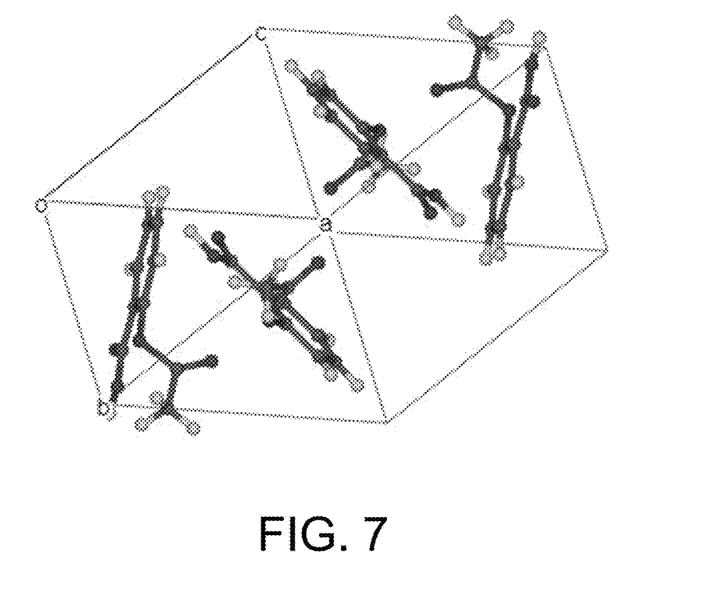
Figure 8:
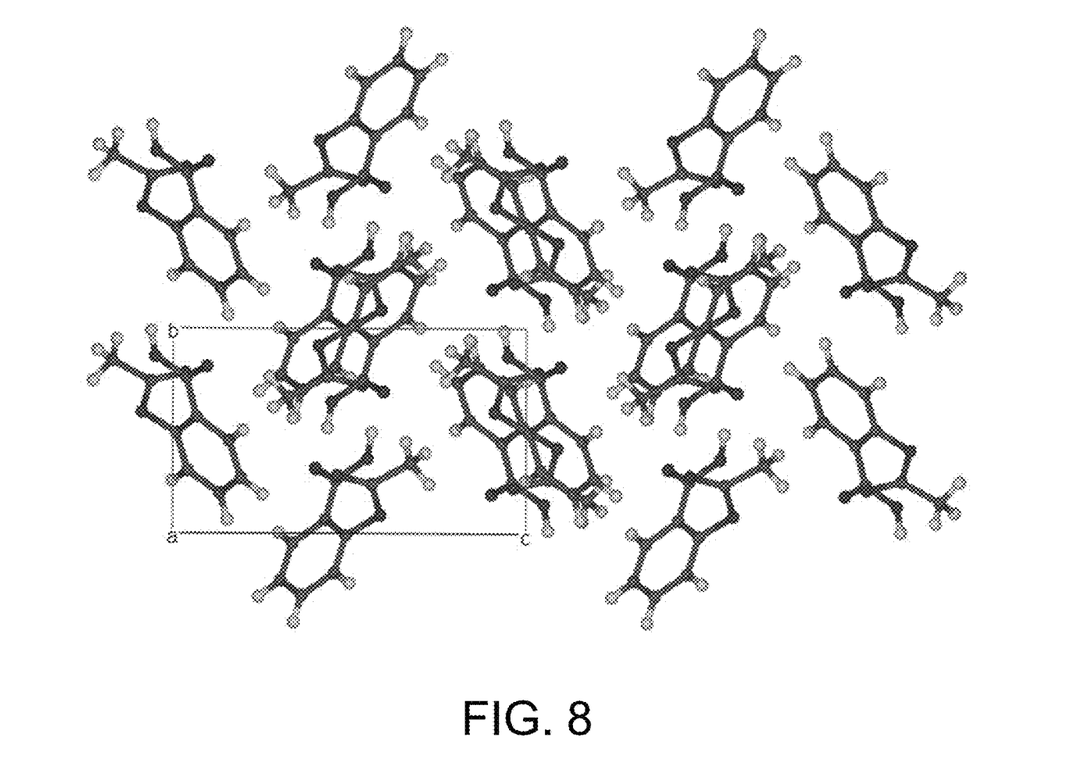
Figure 9:
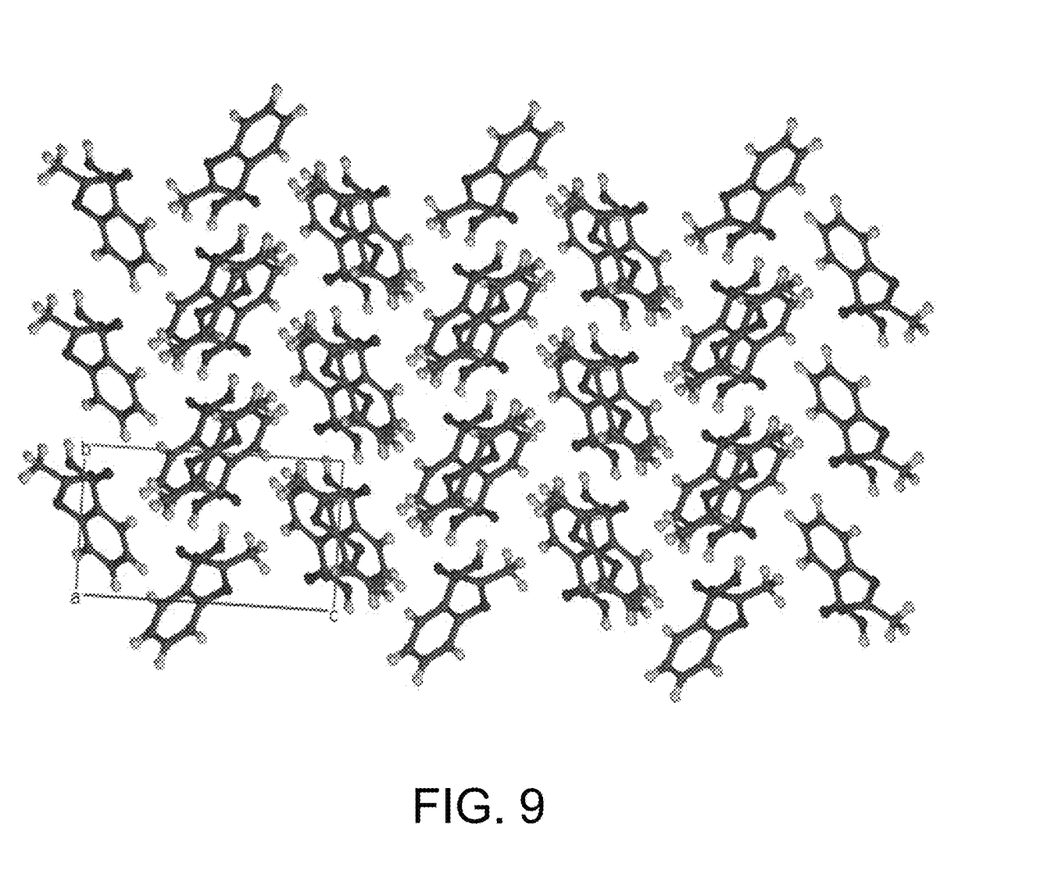

1×1×1: as shown in FIG. 7, 2×2×2 as shown in FIG. 8, and 3×3×3 as shown in FIG. 9.

Description: 3×3×3 lattice expansion is to expand in the three directions of oa, ob, and oc. A single lattice expands into a cube composed of 3×3×3=27 lattices, and 2×2×2 lattice expands into a cube with 8 single lattices.

The effect comparison (using the structure of aspirin for comparison test) is shown in Table 1:

TABLE 1

| Comparison item | Molecular visualization ray method model picking scheme (Ball-and-stick model) | Optimized molecular visualization model picking scheme (Stick-shaped model) |
|---|---|---|
| Non-stacked unit program execution time in a single lattice | 880 ms | 778 ms |
| Execution time for expanding the program in a 1 × 1 × 1 lattice | 1106 ms | 897 ms |
| Execution time for expanding the program in a 2 × 2 × 2 lattice | 1841 ms | 945 ms |
| Execution time for expanding the program in a 3 × 3 × 3 lattice | 3710 ms | 1107 ms |
| Rendering frame rate in a 1 × 1 × 1 lattice | 59.9 fps | 59.9 fps |
| Rendering frame rate in a 2 × 2 × 2 lattice | 59.9 fps | 59.9 fps |
| Rendering frame rate in a 3 × 3 × 3 lattice | 33 fps | 59.9 fps |

Description: 3×3×3 lattice expansion is to expand in the three directions of oa, ob, and oc. A single lattice expands into a cube composed of 3×3×3=27 lattices, and 2×2×2 lattice expands into a cube with 8 single lattices.

The above content is a further detailed description of this invention in combination with specific preferred embodiments, and it cannot be considered that the specific implementation of this invention is limited to these descriptions. For the ordinary technical staff in the technical field of this invention, a number of simple deductions or substitutions can be made without departing from the concept of this invention, which should be regarded as falling within the protection scope of this invention.

What is claimed is:

1. A system for user interaction in complex web 3D scenes, comprising:
   a receiving module;
   a transmission module; and
   a three-dimensional (3D) model module, wherein
   the receiving module is configured to receive molecular data,
   the transmission module is configured to analyze the received molecular data and transmit the received molecular data to a first branch module and a second branch module at the same time,
      wherein the first branch module comprises a view layer unit configured to handle rendering on a browser and construct a 3D model, and present data generated by the first branch module on the browser,
      wherein the second branch module comprises a data layer unit configured to process 3D picking-related business logic, and establish a list of related model index information on atoms and covalent bonds in the molecular data; and
   the 3D model module is configured to establish a one-to-one correspondence between a color and the 3D model, and all 3D models that need to be picked up have a unique index in a data layer, wherein the unique index is a hexadecimal color without rendering on the browser;
   wherein the system comprises a processor and a memory comprising instructions executed by the processor;
   wherein the receiving module, the transmission module, and the 3D model module are executed by the processor.

2. A method for user interaction in complex web 3D scenes, comprising:
- analyzing molecular data after receiving the molecular data;
- transmitting the molecular data to two branch modules at the same time, the two branch modules comprising a first branch module and a second branch module, wherein
  - the first branch module serves as a view layer, processing browser rendering and constructing a 3D model, and the data generated by the first branch module will finally be presented on a browser page;
  - the second branch module serves as the data layer for processing 3D pickup-related business logic, and establishing a list of related model index information on atoms and covalent bonds in the molecular data;
- establishing corresponding simplified model data in an invisible 3D scene, and
- establishing a one-to-one correspondence between a color and the 3D model, all 3D models that need to be picked will have a unique index in the data layer, wherein the unique index is a hexadecimal color without rendering on the browser page.

3. The method according to claim 2, wherein the index is a hexadecimal color, which ranges from #000001 to #FFFFFE that marks a total of 16*16*16*16*16*16-2 units.

* * * * *